US006210875B1

(12) United States Patent
Patterson et al.

(10) Patent No.: US 6,210,875 B1
(45) Date of Patent: Apr. 3, 2001

(54) PROCESS OF DETERMINING THE EFFICACY OF DRUG TREATMENT IN HIV INFECTED SUBJECTS

(75) Inventors: Bruce K Patterson; Victoria Mosiman, both of Chicago; Charles Goolsby, Winfield, all of IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/117,076

(22) PCT Filed: Aug. 22, 1997

(86) PCT No.: PCT/US97/14870

§ 371 Date: Jul. 23, 1998

§ 102(e) Date: Jul. 23, 1998

(87) PCT Pub. No.: WO98/07888

PCT Pub. Date: Feb. 26, 1998

Related U.S. Application Data

(60) Provisional application No. 60/024,404, filed on Aug. 22, 1996, and provisional application No. 60/028,169, filed on Oct. 11, 1996.

(51) Int. Cl.⁷ .................................................. C12Q 1/70
(52) U.S. Cl. ................... 435/5; 435/6; 435/7.1; 435/29; 435/968; 435/974; 424/154.1; 536/24.3; 536/25.32
(58) Field of Search ...................... 435/5, 6, 7.1, 29.968, 435/974; 935/1, 3, 19, 76, 77, 78; 424/154.1; 536/24.3, 25.32

(56) References Cited

U.S. PATENT DOCUMENTS 5,141,923 * 8/1992 Byers et al. ........................... 514/12
5,543,303   8/1996 Goyert ................................ 435/69.1

FOREIGN PATENT DOCUMENTS

WO 93/23574   11/1993  (WO).
WO 96/14437   5/1996   (WO).

OTHER PUBLICATIONS

Suzuki et al. "Characterization of HIV–Related Periodontitis in AIDS Patients: HIV–Infected Macrophage Exudate in Gingival Crevicular Fluid as a Hallmark of Distinctive Etiology", Clinical And Experimental Immunology, vol. 108, No. 2 (1997), pp. 254–9.*
Bernstein et al.. "The Timing and Development of Codon 215 Mutations in Plasma, CD4, and CD14 Cells From HIV–Infected Patients on Zidovudine", Second National Conference on Human Retroviruses and Related Infections, (1995), p. 140, RC583.C54.*
Aoki et al., *Sixth International Conference on AIDS*, 3, S.B.475 (1990).
Bagnarelli et al., *J. Clin. Microbiol.*, 33 (1), 16–23 (1995).
Borvak et al., *J. Immunol.*, 155 (6), 3196–3204 (1995).
Clark et al., *J. Acquir. Immune Defic. Syndr.*, 5 (1), 52–59 (1992).
Davison et al., *J. Clin. Pathol.*, 47, 855–857 (1994).
Donovan et al., *J. Acquir. Immune Defic. Sundr.*, 7, 1237–1241 (1994).
Eron et al., *Proc. Natl. Acad. Sci. USA*, 89, 3241–3245 (1992).
Escaich et al., *J. Acquir. Immune Defic. Syndr.*, 5, 829–834 (1992).
Fleury V, *The Lancet*, 880–881 (Apr. 16, 1988).
Furtado et al., *J. Virol.*, 69, (4), 2092–2100 (1995).
Holodniy et al., *J. cellular Biochem.*, Suppl. 15E, M145 (1991).
Lawrence et al., *Proc. Natl. Acad. Sci. USA*, 87, 5420–5424 (1990).
Lewis V, *Prog. Med. Virol.*, 40, 19–47 (1993).
Michael et al., *J. Virol.*, 66 (1), 310–316 (1992).
Nielsen et al., *AIDS*, 10, 625–633 (1996).
Saksela et al., *Proc. Natl. Acad. Sci. USA*, 91, 1104–1108 (1994).
Schnittman et al., *Science*, 245, 305–308 (1989).
Somasundaran et al., *J. Cell Biol.*, 126, 1353–1359 (1994).
Spadoro et al., *BioTechniques*, 9 (2), 186–195 (1990).
Ved Brat et al., *AIDS Res. Human Retroviruses*, 8, (7), 1271–1281 (1992).
Bagasra et al., *HIV–1 and Monocytes*, 9 (1), 69–76 (1993).
Bauman et al., *Cytometry*, 9, 517–524 (1988).
Belloc et al., *Cytometry*, 14, 339–343 (1993).
Borzi et al., *Journal of Immunological Methods*, 193, 167–176 (1993).
Innocenti et al., *AIDS Research and Human Retroviruses*, 8, (2), 261–268 (1992).
McElrath et al., *J. Chin. Invest.*, 87, 27–30 (1991).
Pajor et al., *Histochemistry*, 96, 73–81 (1991).
Patterson et al., *Cytometry*, 31, 265–274 (1998).
Patterson et al., *Journal of Virology*, 69 (7) 4316–4322 (1995).
Patterson et al., *Science*, 260, 976–979 (1993).
Pennline et al., *Lymphokine and Cytokine Research*, 11 (1) 65–71 (1992).
Ravichandran et al., *Journal of Immunological Methods*, 153, 249–259 (1992).
Timm et al., *Biofeedback*, 12 (3), (1992).
Yu et al., *Nucleic Acids Research*, 20 (1), 83–88 (1991).

* cited by examiner

Primary Examiner—Jeffrey Stucker
(74) Attorney, Agent, or Firm—Leydig, Voit & Mayer, Ltd.

(57) ABSTRACT

The present invention provides a process for determining the efficacy of anti-viral therapy in an HIV-infected subject receiving such therapy. The process includes the steps of a) detecting the level of transcriptionally active HIV in monocytes of the subject at a plurality of different times, b) comparing the detected HIV levels, and c) correlating changes in the detected HIV levels over time with the therapy. The process can be used to monitor the efficacy of treatment with any anti-HIV agent such as AZT, 3TC, DDC, Indivar, or Saquinavir. Decreases in HIV levels over time indicate an efficacious treatment. Increases in detected HIV levels over time indicate resistance to treatment.

10 Claims, 3 Drawing Sheets

PROCESS OF DETERMINING THE EFFICACY OF DRUG TREATMENT IN HIV INFECTED SUBJECTS

CROSS-REFERENCE TO RELATED APPLICATION

The present application is the national stage application of international application PCT/US97/14870, filed Aug. 22, 1997, which designates the United States, a continuation in part of U.S. Provisional Patent Application Ser. No. 60/024,404, filed Aug. 22, 1996 and a continuation-in-part of U.S. Provisional Patent Application Ser. No. 60/028,169, filed Oct. 11, 1996.

TECHNICAL FIELD OF THE INVENTION

The field of the present invention is HIV therapy. More particularly, the present invention pertains to a process of determining the efficacy or efficiency of drug treatment in HIV infected subjects by determining the level of HIV in monocytes of the subject.

BACKGROUND OF THE INVENTION

HIV is known to productively infect a variety of different cell types in vitro and in vivo. The extent to which HIV infects and replicates in these cells has important implications concerning dissemination from portals of entry, cell function, and disease progression given the finite number of target cells. End products of viral replication including expression of unspliced HIV mRNA and plasma free virus has led to virologic determinants as a measure of disease state and therapeutic efficacy. A marked increase in the ratio of unspliced to spliced HIV mRNA as might occur during the shift from latent to productive infection precedes precipitous drops in CD4 count. Plasma viral load has been shown to correlate with disease progression and has been used to determine HIV kinetics in viva. These measurements, however, fail to provide information on the cell type of origin-a weakness considering the effects of HIV expression on cell function, the role of infected cells in transmission and dissemination, and the therapeutic potential of blocking cell type specific co-receptors.

Plasma viral burden analysis have allowed researchers to estimate kinetic parameters of HIV-1 life cycle in vivo. The life span of productively infected T-lymphocytes was estimated to be 2.2 days. The detection and quantification of productively infected lymphocytes, therefore, is technically difficult requiring very sensitive techniques. Further, the turnover of these cells may be too rapid to measure these cells on a continuous basis. In addition, the contribution of free virus to the infective pool by cell types not destroyed by viral replication has not been experimentally addressed and has only been included as an aside in most kinetic models.

The transmission of HIV characteristically involves the early appearance of NSI (non-syncitial inducing), macrophage tropic viral isolates despite the presence or absence of SI (syncitial inducing) and NSI variants in the donor. Effective anti-HIV immune responses have been suggested to temper the replication of SI variants after transmission. Following seroconversion, SI variants start to appear as a result of immune dysfunction. Some studies, however, suggest that NSI, macrophage tropic isolates persist throughout the disease course in spite of the abundance of SI variants.

Recent data lends support to the model that selective transmission may occur as the virus penetrates mucosal surfaces and encounters cells of monocyte/macrophage lineage. The virus can then be distributed throughout the lymphoid system and tissue compartments via these cells. Once in the lymphoid compartment, the virus encounters the overwhelming majority of the body's lymphocytes. The virus accumulates in and eventually destroys the T-cell reservoir leaving only macrophages in T-cell depleted lymph nodes. Although free virus determinations have helped define HIV-1 kinetics in vivo, resent elucidation of macrophage and T-cell tropic coreceptors demands further characterizations of the cells producing virus at various times during disease progression and during antiretroviral therapy.

BRIEF SUMMARY OF THE INVENTION

The present invention provides a process of determining or monitoring the efficacy of drug treatment in HIV infected subjects. In accordance with this process, the levels of HIV RNA in monocytes of the subject are measured over the course of treatment with one or more drugs (e.g., AZT, 3TC, DDC). As drug treatment efficacy increases, the levels of HIV RNA in monocytes decreases. Conversely, where a subject develops resistance to a drug, that resistance is evident from an increase or lack of decrease in monocyte HIV RNA levels. In other words there is a direct correlation between the effectiveness of treatment and monocyte HIV RNA levels. Preferred monocytes for use in this invention are $CD14^+$ monocytes.

In accordance with the present invention, dual immunophenotyping PCR in situ hybridization (DIPDISH) is used to detect cells containing HIV-1 DNA, dual immunophenotyping fluorescence in situ hybridization (DIPFISH) is used to detect and quantify gag-pol mRNA in cells and quantitative RNA analysis is used to quantify plasma viral load. The present invention discloses that monocytes, and particularly $CD14^+$ monocytes, are persistently productive of HIV message. Furthermore, the levels of HIV mRNA in those monocytes respond in parallel with plasma viral load to drug therapy. As viral message production is an earlier event in virion production a process of the present invention is more a more sensitive indicator of drug efficacy and drug resistance than prior art methods.

Productively infected cell types in patients infected by HIV have been identified and quantified. As shown previously, very few CD4 positive lymphocytes were productively infected by HIV although many contain proviral DNA. The present invention discloses that monocytes are the major productively infected cell type in HIV seropositive individuals and viral production in these cells is altered by antiretroviral therapy. The percentage of productively infected monocytes corresponded with viral burden analysis in patients on no, single, combination, and triple drug therapy.

BRIEF DESCRIPTION OF THE DRAWINGS

In the drawings, which form a portion of the specification.

DETAILED DESCRIPTION OF THE INVENTION

Figure 1:
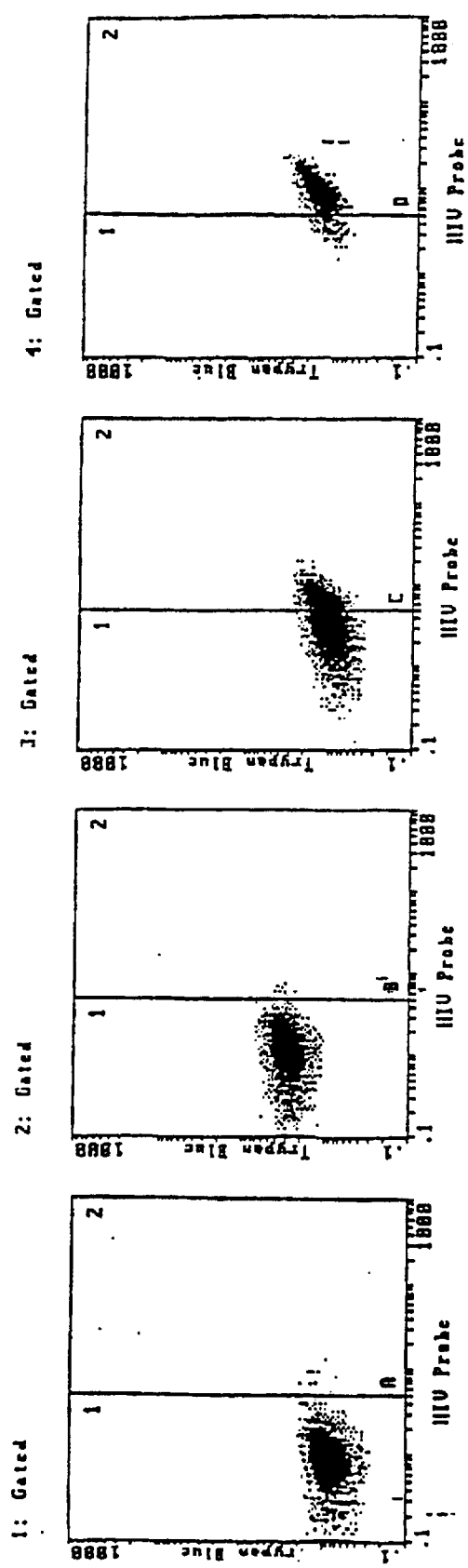
FIG. 1 shows a time course experiment of ACH-2 cells stimulated with TNF-α and detected using FISH. Less than 5 percent of the cells express any HIV-1 mRNA at time point 0 (A), expression of HIV-1 multiply spliced mRNA is produced within 1 hour (B) and unspliced transcripts start to be produced at the 12 hour timepoint (C), and expression of all mRNA is seen in over 90% of the stimulated cells at 24 hours (D). The ACH-2 cell line (AIDS Research and Reagent Program, NIAID, NIH Bethesda, Md.), containing a single copy of integrated HIV-1 proviral DNA per cell, was harvested at an early passage number and used as the HIV-1 infected cell copy number control cells were stimulated with μg/ml TNF-α.

The present invention provides a process for determining the efficacy of anti-viral therapy in an HIV-infected subject receiving such therapy. The process includes the steps of a) detecting the level of transcriptionally active HIV in monocytes of the subject at a plurality of different times, b) comparing the detected HIV levels, and c) correlating changes in the detected HIV levels over time with the therapy. The process can be used to monitor the efficacy of treatment with any anti-HIV agent such as AZT, 3TC, DDc, Indivar, or Saquinavir. Decreases in HIV levels over time indicate an efficacious treatment. Increases in detected HIV levels over time indicate resistance to treatment.

The level of transcriptionally active HIV is detected by measuring the level of HIV mRNA and, preferably gag-pol HIV mRNA. The HIV mRNA is detected using in situ hybridization. In situ hybridization is accomplished by exposing monocytes in situ to an oligonucleotide probe that specifically hybridizes to at least of a portion of the HIV mRNA. The probe is labeled with a detectable marker, the detection of which indicates the presence of HIV mRNA.

A process of this invention is particularly useful when the monocytes harboring the transcriptionally active HIV are CD14$^+$ monocytes. CD14$^+$ monocytes are identified in blood samples of the subject using immunophenotyping. In accordance with such immunophenotyping, a blood sample is exposed to an antibody directed against CD14$^+$, which antibody is labeled with a detectable marker. In a preferred embodiment, the immunophenotyping and in situ hybridization are carried out simultaneously. In accordance with that preferred embodiment, CD14$^+$ is labeled with an anti-CD14$^+$ antibody having a first detectable label attached thereto, the labeled monocytes are then fixed and permeabilized in the presence of an oligonucleotide probe that hydridizes to the HIV mRNA, which probe is labeled with a second detectable marker, and the amount of both detectable labels measured. Preferably, the first and second detectable labels are fluorescent labels. A preferred first detectable label is phycoerythrin. A preferred second detectable label is 5- or 6-carboxyfluorescein.

The level of HIV RNA in monocytes is determined in blood samples from the subject using a combination of cellular antigen (e.g., CD14) detection (using labeled antibodies) and in situ hybridization using a tagged probe directed against a region of HIV RNA. Details of such methods are set forth below. A detailed description of simultaneous in situ cellular antigen detection and nucleic acid amplification can be found in U.S. Pat. No. 5,843,640, filed Aug. 30, 1995, the disclosure of which is incorporated herein by reference.

Study subjects

Thirty-seven HIV seropositive patients from the VA Lakeside Hospital followed routinely were evaluated using CD4 count, DIPDISH, DIPFISH, and quantitative RNA analysis. Ten HIV seronegative patients were evaluated using the same assays. Patients were either on no therapy, single drug therapy with AZT (200 mg, three times a day) or DDC (0.75 mg, three times a day), combination therapy with AZT and 3TC (150 mg, two times a day), or triple therapy with AZT 3TC and either Indinavir (800 mg, three times a day) or Saquinavir (600 mg, three times a day). All patients were on therapy for at least 30 days prior to blood donation.

Histogram gates were set based on a negative control cocktail directed against cytomegalovirus and on a positive control cocktail directed against 28 ribosomal RNA. Fine tuning of the gates on each patient sample were set based on internal HIV-negative and CD4 or CD14 negative populations. CD4$^+$ T-lymphocytes containing HIV-1 DNA ranged from 4% to 43%. The percentage of cells containing HIV-1 DNA did not correlate with CD4 count or drug therapy suggesting that this population may be a reservoir for defective viral genomes, nonproductive infection of resting T-cells, or provirus capable of subsequent activation.

Cells and cell lines

PBMCs were isolated from fresh heparinized blood layered on a Histopaque 1077 (Sigma, St. Louis, Mo.) discontinuous density gradient and centrifuged at 600×g for 30 minutes at ambient temperature. The turbid layer was removed, washed twice with 3 volumes of RPMI and once with phosphate buffered saline (PBS). The ACH-2 cell line (AIDS Research and Reagent Program, NIAID, NIH, Bethesda, Md.), containing a single copy of integrated HIV-1 proviral DNA per cell, was harvested at an early passage number and used as the HIV-1-infected cell copy number control.

Dual Immunophenotyping/Fluorescence in situ Hybridization (DIPFISH).

To determine the cell types containing HIV RNA using DIPFISH, cells were labeled with optimized concentrations of phycoerythrin (PE)-conjugated antibodies specific for the cell types of interest (CD4, CD14) and fixed and permeabilized by the addition of 50 µl of a water-soluble, non-aldehyde fixative, Permeafix (Ortho Diagnostics, Inc.) per $10^6$ cells at ambient incubation temperature for at least 60 min. The cells were then washed twice in PBS, pH 7.4 at ambient temperature and once in 2×SSC at ambient temperature.

The cells were then resuspended with 50 µl hybridization buffer containing a cocktail of 5- or 6-carboxyfluorescein-labeled oligonucleotides specific for HIV RNA. Positive (ribosomal RNA) and negative control cocktails were used in replicate samples. Probe was hybridized to target for 30 minutes at 43° C. in a water bath. The cells were washed with buffer at 42° C. Autofluorescence was quenched using quenching reagent. Multiparameter analysis of cell surface molecules and HIV RNA was performed on a Coulter XL flow cytometer (Coulter, Hialeah, Fla.).

Dual Immunophenotyping/PCR-driven in situ hybridization (DIPDISH).

Cell samples were adjusted to a final concentration of $1 \times 10^6$ cells/mi. A 400 µl aliquot of each sample was centrifuged at 600×g for 2 minutes at ambient temperature and the cell pellet was washed twice in PBS. The cells were then fixed and permeabilized by the addition of 50 µl of Permeafix (Ortho Diagnostics, Inc.) at ambient temperature for 60 minutes. Cells were then pelleted as above, washed with PBS and resuspended in 190 µl of PCR reaction mixture consisting of 10 mM Tris HCL (pH 8.3); 50 mM KCL; 1.5 mM $MgC_4$; 0.25 mM each dATP, dCTP, dGTP; 0.14 mM dTTP; 4.3 µM dUTP-11-digoxigenin; 100 pmole each forward and reverse primer; 1.0 µl (5 Units) Taq polymerase (Amplitaq, Perkin-Ehner, Norwalk Conn.); and gelatin 0.001% w/v.

The DNA in the reaction mixture was amplified in 500 µl tubes inserted into the wells of a 48 well thermocycler (Perkin-Elmer Cetus) programmed for 25 cycles of thermal denaturation (94° C., 1 minute), primer annealing (58° C., 2 minutes), and primer extension (74° C., 1.5 minutes), with 5 seconds added for each of 25 cycles. Appropriate positive and negative controls amplified with or without the addition of Taq polymerase were simultaneously run with each sample. After amplification, cells were pelleted and resuspended in 25 µl of 10 mM Tris HCL (pH 8.3), 50 mM KCL, and 1.5 mM $MgC_4$. A 100 mg aliquot of the appropriately labeled target specific oligonucleotide probe in 10 µg/ml sonicated herring sperm DNA (Sigma) was added to the reaction tube. The product DNA was denatured at 95° C. for 3 minutes then allowed to hybridize with the respective oligonucleotide probe at 56° C. for 2 hours.

After hybridization, the cells were washed for 30 minutes with 2×SSC/50% formamide/500 µg/ml bovine serum albumin (BSA) at 42° C., 30 minutes with 1×SSC/50% formamide/500 µg/ml BSA at 42° C., 30 minutes with 1×SSC/500 µg/ml BSA at ambient temperature and then briefly with PBS at ambient temperature. Following the last wash, the cells were resuspended in 80 µl of PBS and 20 µl strepavidin-phycoerythrin (PE) and incubated for 30 minutes at ambient temperature. The cells were then washed in PBS as described above.

Flow Cytometry.

The cell suspension was filtered through a 37 mm nylon mesh and analyzed by flow cytometry using an EPICS XL flow cytometer. Laser excitation was 15 mW at 488 nm, and the FITC and PE florescence was detected with standard optical filter set-up (550 dichroic, 525 bandpass (FITC) and 585 bandpass (PE)). Instrument sensitivity was standardized before each experiment employing Immuno-Bright calibration beads (Coulter Source, Marriette, Ga.). The percent fluorescence-positive cells was determined by integration over a range of 0.2% positive counts on the identically treated negative sample (100% uninfected PBMCs).

Viral Burden.

Quantitative RNA determinations were performed on plasma using the Amplicor RNA kit (Roche Molecular Systems, Alameda, Calif.) as per manufacturer instructions.

In peripheral blood, a significant proportion of PBMCs contain HIV-1 DNA while very few contain transcriptionally active virus. Simultaneous immunophenotyping not only allowed unequivocal identification of infected cell subtypes but also enriched cell subtypes for the various infected cell types present in the blood. To determine the cell types with productive or latent HIV infection, immunophenotyping was combined with a novel in situ hybridization strategy using 220 5'- and 3', 6-carboxyfluorescein-labeled oligonucleotides complementary to gag-pol targets or with in situ PCR for proviral DNA. The in situ hybridization experiments were calibrated using the ACH-2 cell line with and without TNF-α stimulation. Time course experiments (FIG. 1) reveal that >98% of unstimulated ACH-2 cells express high levels of HIV-1 mRNA which agrees with previous estimates. Twenty four hours following stimulation, >90% of ACH-2 cells express high levels of HIV-1 mRNA which corresponds to between 300–400 genome copies per cell.

Figure 2A:
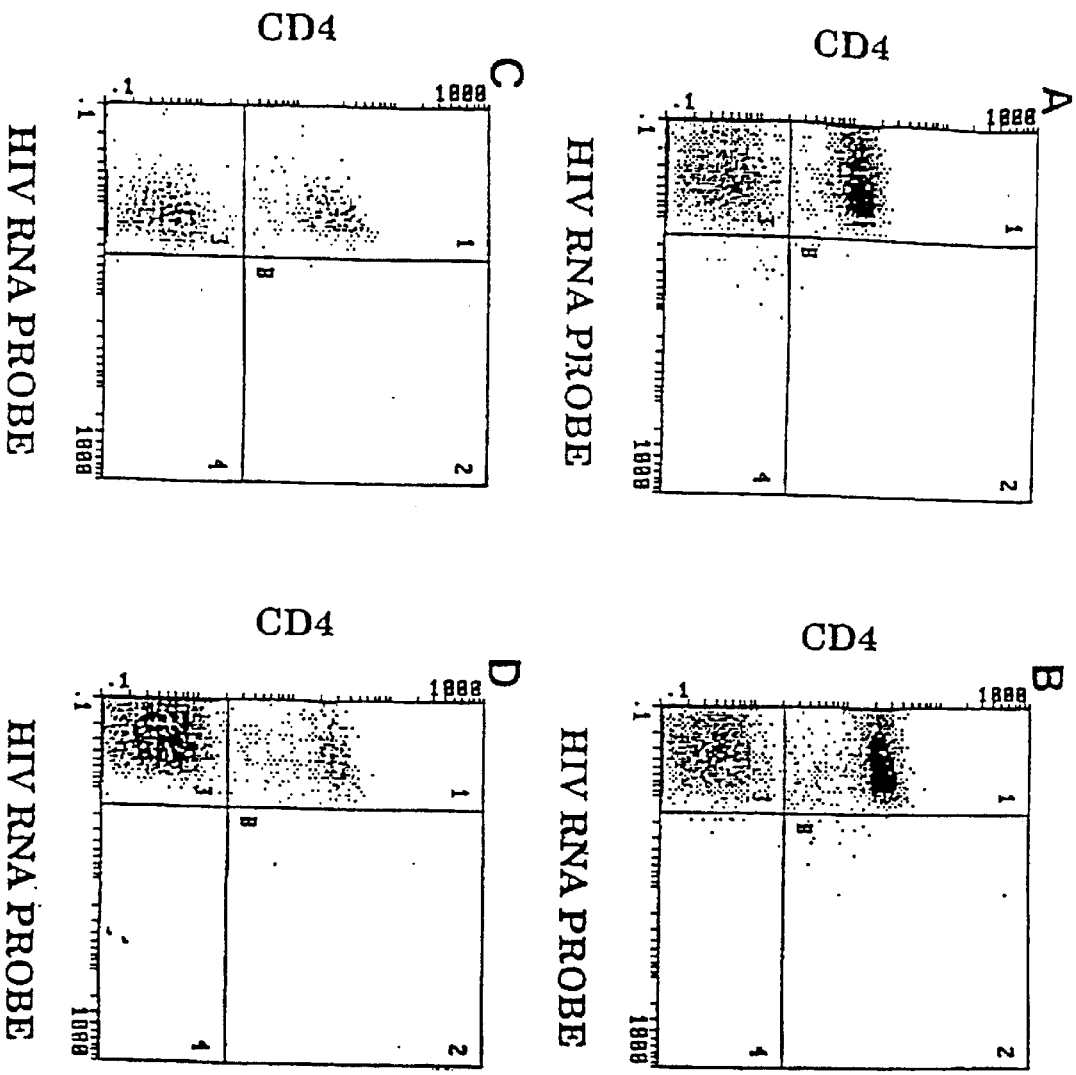
FIG. 2a shows dot plots of patient PBMCs following DIPFISH. To determine the cell types containing HIV RNA using DIPFISH cells are labeled with optimized concentrations of phycoerythrin conjugated antibodies specific for the cell types of interest (CD4, (FIG. 2a), CD14 (FIG. 2b)) and fixed and permeabilized by the addition of 50 µl of Permeafix (Ortho Diagnostics, Inc.) per $10^6$ cells at ambient incubation temperature for at least 60 minutes. The cells are then washed twice in PBS, pH 7.4 at ambient temperature and once in 2×SSC at ambient temperature. The cells are then resuspended with 50 µl hybridization buffer containing a cocktail of 5- or 6-carboxyfluorescein-labeled oligonucleotides specific for HIV RNA-Positive (ribosomal RNA) and negative control cocktails are used in replicate samples. Probe was hybridized to target for 30 minutes at 43° C. in a water bath. The cells were washed for 5 minutes with buffer A at 42° C., 30 minutes with buffer B at 42° C. Autofluorescence was quenched using quenching reagent. Multiparameter analysis of cell surface molecules and HIV RNA was performed on a Coulter XL flow cytometer (Coulter, Hialeah, Fla.).
Figure 2B:
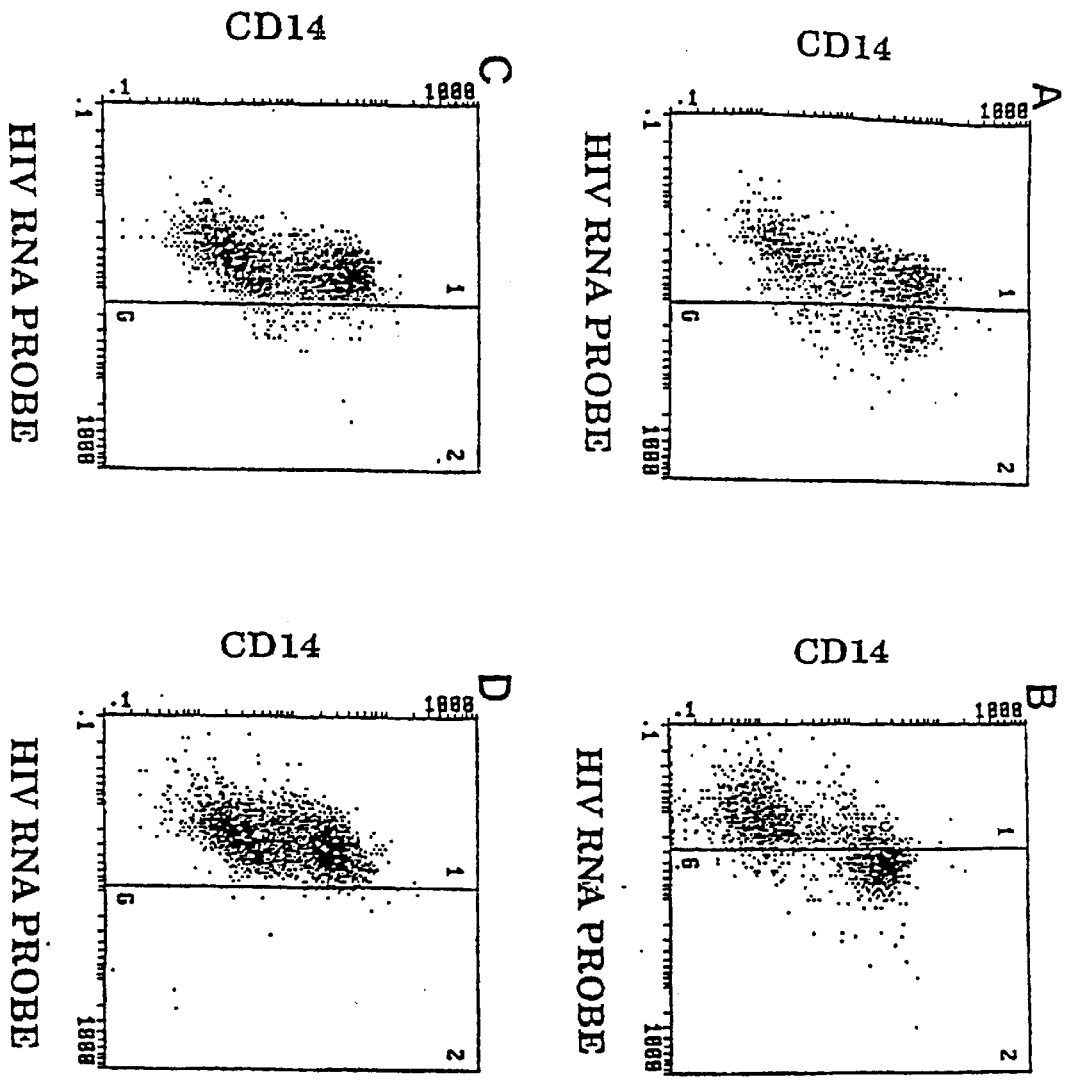
FIG. 2b shows a scattergram illustrating the relationship of productively infected monocytes (abscissa) and plasma viral load (ordinate) in patients on no ♦, single ■, combination △, and triple × therapy. Forty HIV seropositive patients from the VA Lakeside Hospital followed routinely were evaluated using CD4 count, DIPDISH, DIPFISH, and quantitative RNA. Five HIV seronegative patients were evaluated using the same assays. Patients were either on no therapy, single drug therapy with AZT (200 mg three times/day) or DDC (0.75 mg three times/day), combination therapy with AZT and 3TC (150 mg two times/day), or triple therapy with AZT 3TC and either Indinavir (800 mg three times/day) or Saquinavir (600 mg three times/day). All patients were on therapy for at least 30 days prior to blood donation. PBMCs were isolated from fresh heparinized blood layered on a Histopaque 1077 (Sigma, St. Louis, Mo.) discontinuous density gradient and centrifuged at 600×g for 30 minutes at ambient temperature. The turbid layer was removed, washed twice with 3 volumes of RPMI and once with phosphate buffered saline (PBS).

Using simultaneous immunophenotyping with CD4 and CD14 and in situ hybridization, the data show that a significant proportion of monocytes harbor transcriptionally active HIV whereas very few CD4 T-lymphocytes harbor transcriptionally active virus at any point in time (FIGS. 2a and 2b). The percentage of productively infected monocytes ranged from <1% to 93% percent and the percentage of productively infected CD4 lymphocytes ranged from <1 to 6% which, most likely, represents the more rapid turnover of productively infected CD4 cells and the persistence of productively infected monocytes. It was previously suggested that productive infection of monocytes occurred following differentiation to macrophages and indeed a significant proportion of cells were found in peripheral blood with the CD14 low, CD16 high phenotype indicative of macrophage differentiation. Backgating on the cells expressing HIV RNA, however, did not reveal a specific, infected subset of CD14 positive cells.

To determine the relationship between the percentage of infected cells and plasma viral load, plasma was obtained from the same sample used to isolate PBMCs and quantitative competitive RNA PCR was performed on each sample (FIG. 3). Six groups were identified: those patients with high viral load, high percentage of infected monocytes; high viral load, low percentage of infected monocytes; low viral load, high percentage of infected monocytes; low viral load, low percentage of infected monocytes; and intermediate or low viral load, intermediate percentage of infected monocytes. A low viral load in the presence of a high percentage of monocytes expressing HIV-1 mRNA may represent early indication of drug resistance. A high viral load in the presence of a low percentage of monocytes expressing HIV-1 mRNA may represent production of free virus predominantly in other cell types as may occur in the phenotypic switch preceding symptomatic infection. Even in the extreme cases of a patient with a high viral titer in spite of triple therapy or a patient with a low viral titer in the absence of therapy, the percentage of infected monocytes paralleled the viral load.

Nine out of fifteen patient (60.0%) with a high percentage of monocytes expressing HIV-1 mRNA had viral loads over 50,000 copies/ml while four out of twenty-three patient (17%) with less than 50% monocytes expressing HIV-1 mRNA had viral loads over 50,000 copies/ml. As viral message production is an earlier event in the viral lifecycle, this measurement is likely a more sensitive indicator of drug efficacy and drug resistance.

Productively infected cell types in blood from patients infected by HIV were identified and quantified. CD14 positive monocytes were the major persistently productive cells infected with HIV. A specific subtype of infected monocytes was not identified even though CD14 low, CD16 high cells phenotypically resembling macrophages have been identified in the peripheral blood of HIV seropositive individuals. Interestingly, productively infected monocytes in several patients exhibited an increased CD14 mean peak fluorescence relative to the HIV negative monocytes in the same sample. Increases in CD14 expression in monocytes has been shown in the peripheral blood of HIV-infected patients although the presence of HIV in these cells was not determined in this previous study. CD14 is a glycosyl-phosphatidynositol-anchored molecule on the surface of monocytes and to a lesser extent granulocytes. Monocyte activation by lipopolysaccharide requires CD14, therefore alterations of CD14 could conceivably explain the functional defect of monocytes at the cellular level in HIV-infected individuals. As shown previously, very few CD4 positive lymphocytes were productively infected by HIV although many contain proviral DNA.

The transmission of HIV involves the early infection of antigen presenting cells such as Langerhans cells and monocytes following breach of mucosal barriers. Virus is shuttled in these cells via peripheral blood to lymphoid and other tissue. Within lymphoid tissue free virus produced by productively infected cells can infect other permissive cells or become trapped within the follicular dendritic cell (FDC) network.

Following infection, non-syncytium-inducing (NSI), macrophage tropic viral isolates predominate despite the presence or absence of syncytium-inducing (SI) and NSI variants in the donor. Effective anti-HIV immune responses have been suggested to temper the replication of SI variants after transmission. Following progression to symptomatic disease, SI variants start to appear as a result of immune dysfunction. The studies herein show that cells of the monocyte/macrophage lineage are likely a major reservoir of virus capable of producing virions. Yet this reservoir has been omitted from mathematical models proposed to examine the relationship between virion production and host cell destruction.

Much debate has centered on the question of whether monocytes are infected, productively or latently, by HIV in vivo. The absolute monocyte count and the absolute CD4 count were calculated in all of the patients. Based on the percentage of productively infected CD4 T-lymphocytes and productively infected monocytes, and given that monocytes release anywhere from 10% to 50% of the number of virions as T-cells, the amount of free virus contributed by these cell types should be roughly equivalent. The exception to this would be patients with high viral loads and a low percentage of infected monocytes (FIG. 3). These patients were all symptomatic with CD4 counts less than 200 suggesting the switch to the T-cell tropic, SI phenotype had occurred in these patients. This may explain why other studies in patients with AIDS indicate that monocytes are rarely a source of virus.

Quantification of infected monocytes/macrophages is not only critical for a complete kinetic model of HIV infection but also for therapeutic monitoring. Since these cells are not destroyed by viral production and persistently infected cells such as macrophages, may have a lifespan five to six times longer than infected T-lymphocytes, these cells are ideal for monitoring HIV activity at the cellular level including lymphoid tissue such as tonsil and lymph nodes.

Clearly, the contribution of productively-infected monocytes to the free virus pool must be distinctly defined. With the discovery of new tropism dependent co-receptors for HIV and inevitable therapy directed at blocking these co-receptors, determination of productively infected cell types and their contribution to the free virus pool is critical. The ease of the technologies used to define the viral lifecycle in this study most likely portends the end of surrogate markers as we know them and reaffirms the trend toward viral lifecycle monitoring.

What is claimed is:

1. A process for determining the efficacy of anti-viral therapy in an HIV-infected subject receiving such therapy, the process comprising the steps of:

a) detecting the level of transcriptionally active HIV in monocytes of the subject at a plurality of different times by simultaneously exposing the monocytes to an oligonucleotide probe that specifically binds to at least a portion of HIV mRNA and exposing the monocytes to an antibody, wherein the oligonucleotide probe is labeled with a fluorescent label;

b) comparing the detected HIV levels; and c) correlating changes in HIV levels over time with the therapy to determine the efficacy of the anti-viral therapy is the subject.

2. The process of claim 1 wherein the monocytes are CD14+ monocytes.

3. The process of claim 2 wherein the CD14+ monocytes are labeled with a antibody against CD14, which antibody is labeled with a detectable marker.

4. The process of claim 3 wherein the detectable marker is a fluorescent label.

5. The process of claim 4 wherein the detectable marker is phycoerythrin.

6. The process of claim 1 wherein the portion of HIV mRNA is the gag-pol portion.

7. The process of claim 1 wherein the fluorescent label is a 5- or 6-carboxyfluorescein.

8. The process of claim 1 wherein the anti-viral therapy is selected from the group consisting of treatment with AZT, 3TC, Ddc, Indivar and Saquinavir.

9. The process of claim 1 wherein decreases in HIV-RNA levels over time indicate an efficacious treatment.

10. The process of claim 1 wherein increases in HIV-RNA levels over time indicate resistance to treatment.

* * * * *